United States Patent
Nishihara et al.

(10) Patent No.: US 7,493,818 B2
(45) Date of Patent: Feb. 24, 2009

(54) DROP SHOCK MEASUREMENT SYSTEM AND ACCELERATION SENSOR ELEMENT USED IN THE SAME

(75) Inventors: Kazunari Nishihara, Osaka (JP); Hirofumi Tajika, Osaka (JP); Koji Nomura, Nara (JP); Motoyuki Toji, Kyoto (JP)

(73) Assignee: Panasonic Corporation, Osaka (JP)

( * ) Notice: Subject to any disclaimer, the term of this patent is extended or adjusted under 35 U.S.C. 154(b) by 161 days.

(21) Appl. No.: 10/769,263

(22) Filed: Jan. 30, 2004

(65) Prior Publication Data
US 2004/0182182 A1 Sep. 23, 2004

Related U.S. Application Data

(62) Division of application No. 10/398,138, filed as application No. PCT/JP02/08053 on Aug. 7, 2002, now abandoned.

(30) Foreign Application Priority Data
Aug. 9, 2001 (JP) ............... 2001-242871

(51) Int. Cl.
G01D 21/00 (2006.01)
(52) U.S. Cl. ............... 73/651; 73/514.29
(58) Field of Classification Search ............. 73/514.15, 73/541.16, 514.29, 651
See application file for complete search history.

(56) References Cited

U.S. PATENT DOCUMENTS

| | | | |
|---|---|---|---|
| 4,341,189 A * | 7/1982 | Yamaguchi et al. ............ 73/651 |
| 4,431,935 A * | 2/1984 | Rider ......................... 310/331 |
| 4,625,137 A | 11/1986 | Tomono |
| 4,855,544 A * | 8/1989 | Glenn ................... 200/61.45 R |
| 4,996,878 A * | 3/1991 | Kubler ........................ 73/651 |
| 5,610,337 A * | 3/1997 | Nelson .................... 73/514.29 |
| 6,058,778 A * | 5/2000 | Chan et al. ............... 73/514.16 |
| 6,098,460 A * | 8/2000 | Otsuchi et al. ............ 73/514.34 |
| 6,263,734 B1 | 7/2001 | Fujii et al. |
| 6,282,941 B1 | 9/2001 | Mader |
| 6,343,242 B1 | 1/2002 | Nomura et al. |
| 6,619,123 B2 * | 9/2003 | Gianchandani et al. .. 73/514.29 |

(Continued)

FOREIGN PATENT DOCUMENTS

JP  54-36771 A  3/1979

(Continued)

OTHER PUBLICATIONS

International Search Report for Application No. PCT/JP02/08053 mailed Nov. 26, 2002 with English translation of Form PCT/ISA/210.

*Primary Examiner*—Hezron Williams
*Assistant Examiner*—Nashmiya S Fayyaz
(74) *Attorney, Agent, or Firm*—RatnerPrestia

(57) ABSTRACT

The drop impact measuring system has i) a plurality of bimorph-type acceleration sensor containing a plurality of free vibrating sections each of which has individual draw-out electrodes; ii) a switch section for selecting output from the bimorph-type acceleration sensors; iii) an amplifying circuit for amplifying a signal applied via the switch section from the acceleration sensors; and iv) a logic circuit for logically evaluating the output from the amplifying circuit and controlling the switch section according to the result acquired from the logical evaluation.

5 Claims, 8 Drawing Sheets

U.S. PATENT DOCUMENTS 7,024,738 B2 * 4/2006 Fujii et al. .................. 310/328
2002/0174588 A1 11/2002 Danner et al.

FOREIGN PATENT DOCUMENTS

| JP | 63-304123 A | 12/1988 |
| JP | 05333047 A | 12/1993 |
| JP | 2000-121661 A | 4/2000 |

* cited by examiner

DROP SHOCK MEASUREMENT SYSTEM AND ACCELERATION SENSOR ELEMENT USED IN THE SAME

This application is a divisional of U.S. patent application Ser. No. 10/398,138, filed Aug. 14, 2003, now abandoned which is a U.S. National Phase Application of PCT Application Ser. No. PCT/JP02/08053, filed Aug. 7, 2002.

TECHNICAL FIELD

The present invention relates to a drop impact measuring system used for a drop impact test on mobile electronic equipment including a mobile phone, and also relates to an acceleration sensor element employed for the drop impact measuring system.

BACKGROUND ART

For mobile electronic equipment including a mobile phone, a notebook size computer, a mobile cassette player, compact disc (CD) player, and mini disc (MD) player, drop-down is an ever-present accident when considering its intended use. Accordingly, protecting the equipment from impact caused by the drop-down has now been a growing need. A typical failure comes from distortion of a motherboard mounted on the equipment due to drop-down impact, by which some on-board components have shorts in the wiring, or come off the board. Therefore, to protect the equipment from such accidents, following steps should be taken: i) selecting a material and a structure of electronic equipment to be tested; ii) determining a drop-down height and direction; iii) simulating drop-down impact acceleration applied to each section of the equipment; and then iv) getting feedback from the result and improving the design of the inner structure, for example, the position and method of installing a circuit board. However, the drop-down impact acceleration during falling greatly varies between falling objects, and the acceleration applied to an object has significant magnitude. Furthermore, resonance frequency caused by drop impact greatly depends on the structure of an object. The reasons above have been obstacles to detection of drop-down impact acceleration applied to a falling object.

DISCLOSURE OF THE INVENTION

The drop impact measuring system has i) a plurality of bimorph-type acceleration sensors containing a plurality of free vibrating sections each of which has individual draw-out electrodes; ii) a switch section for selecting output of the bimorph acceleration sensors obtained through the draw-out electrodes; iii) an amplifying circuit for amplifying at least one of voltage and current applied via the switch section from the bimorph acceleration sensors; and iv) a logic circuit for logically evaluating the output from the amplifying circuit and controlling the switch section according to the result acquired from the logical evaluation.

A bimorph acceleration sensor element is formed of the free vibrating sections having cantilever beams. Signals generated at the free vibrating section are fed through the draw-out electrodes to the switch section.

The bimorph acceleration sensor element is also formed of the free vibrating section having both-ends-supported beams. Signals generated at the free vibrating section are fed through the draw-out electrodes to the switch section.

BEST MODE FOR CARRYING OUT OF THE INVENTION

First Exemplary Embodiment

Figure 1:
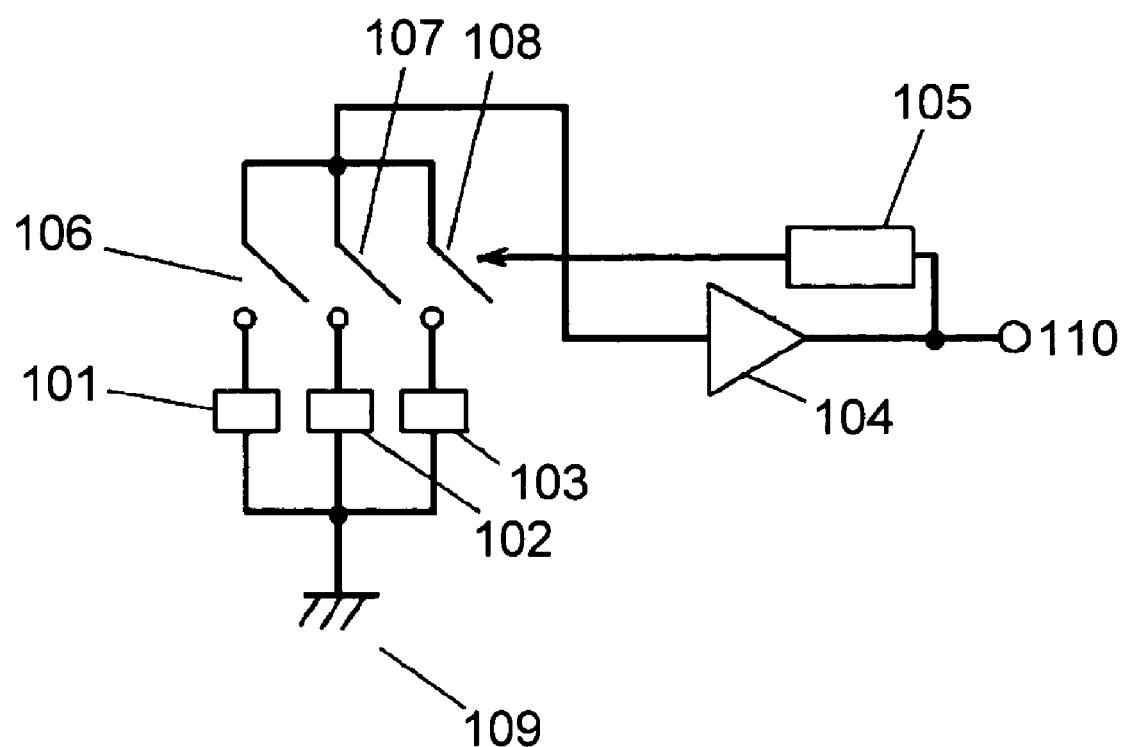
FIG. 1 shows a circuit diagram of a drop impact measuring system in accordance with a first and a second embodiments of the present invention.

FIG. 1 shows a circuit diagram of a drop impact measuring system in accordance with a first embodiment of the present invention. Acceleration sensors 101, 102, and 103 are connected to switches 106, 107, and 108, respectively. Sensors 101 through 103 are also connected to ground 109. By closing one of switches 106 through 108, an output signal from one of acceleration sensors 101 through 103 is fed into amplifying circuit 104 to be amplified. Amplifying circuit 104 outputs a signal, which corresponds to acceleration, via terminal 110. Logic circuit 105 evaluates whether or not the signal from amplifying circuit 104 stays within a predetermined threshold, and whether resonance occurs or not, accordingly outputs logically evaluated result. Logic circuit 105 determines which one of switches 106 through 108 should be closed, according to the logical evaluation, thereby controlling switches 106 through 108.

Figure 5A:
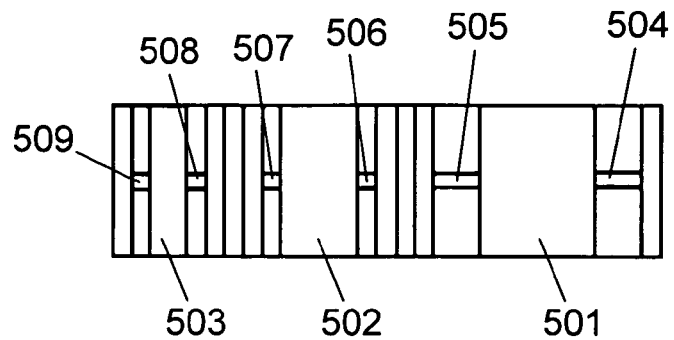
FIG. 5A shows a top view of an acceleration sensor element having a both-ends-supported beam structure in accordance with the first embodiment.
Figure 5B:
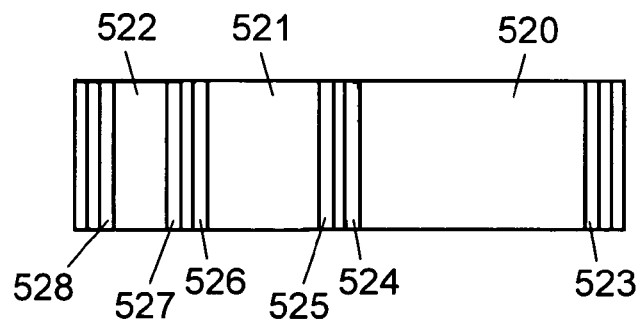
FIG. 5B shows a bottom view of the acceleration sensor element having a both-ends-supported beam structure in accordance with the first embodiment.
Figure 5C:
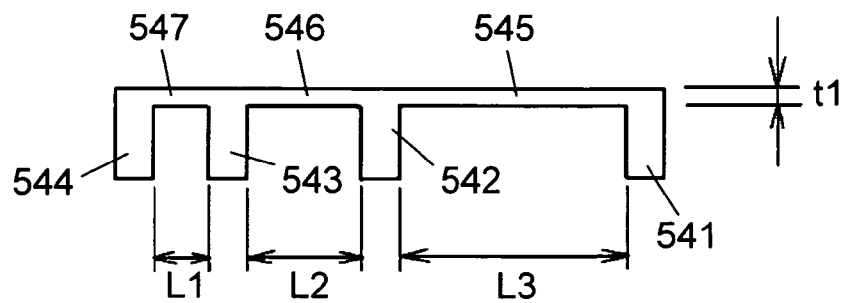
FIG. 5C shows a side view of the acceleration sensor element having a both-ends-supported beam structure in accordance with the first embodiment.
Figure 5D:
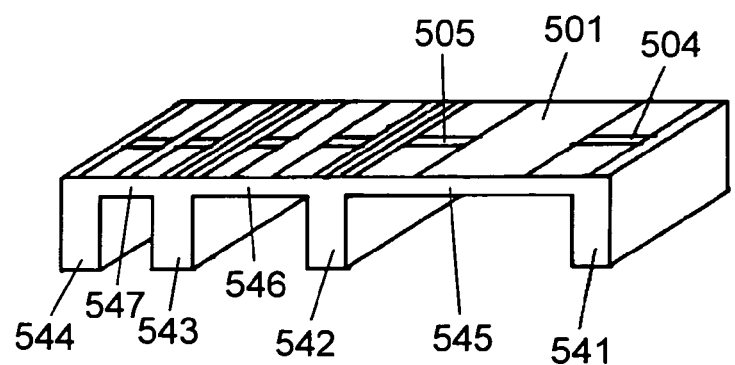
FIG. 5D shows a perspective view of the acceleration sensor element having a both-ends-supported beam structure in accordance with the first embodiment.

FIGS. 5A through 5D show the structure of an acceleration sensor element, which is the major component of acceleration sensors 101 through 103. FIGS. 5A through 5D shows an acceleration sensor element having a both-ends-supported beam structure. FIG. 5A is a top view; FIG. 5B is a bottom view; FIG. 5C is a side view; and FIG. 5D is a perspective view. Each of free vibrating sections 545 through 547 shown in FIGS. 5A through 5D has a bimorph structure in which distortion and vibration occurs when an impactive force is applied. Free vibrating sections 545, 546, and 547 have main electrodes 501, 502, and 503 on each upper surface thereof; and have main electrodes 520, 521, and 522 on each lower surface thereof, respectively. Draw-out electrodes 504 and 505 are connected with main electrode 501; draw-out electrodes 506 and 507 are connected with main electrode 502; and draw-out electrodes 508 and 509 are connected with main electrode 503 to establish electrical connections, respectively. Free vibrating sections 545 through 547 generate electric charges according to distortion in shape due to their bimorph structures. The electric charge generated on each upper surface of free vibrating sections 545, 546, and 547 is carried to main electrodes 501, 502, and 503, respectively, and further carried to draw-out electrodes 504 and 505; 506 and 507; 508 and 509, respectively. On the other hand, The electric charge generated on each lower surface of free vibrating sections 545, 546, and 547 is carried to main electrodes 520, 521, and 522, respectively, and further carried to draw-out electrodes 523 and 524; 525 and 526; 527 and 528, respectively. The electric charges carried to main electrodes 520 through 522 are opposite in polarity to those carried to main electrodes 501 through 503. Draw-out electrodes 523 through 528 are extended to the bottom of supporters 541 through 544, via the side surfaces of the supporters, and are exposed at the bottom of the each supporter.

The deformation of free vibrating sections 545 through 547 creates oppositely polarized electric charges: one is drawn out by draw-out electrodes 504 through 509 disposed on the upper surface of free vibrating sections 545 through 547; the other is drawn out by draw-out electrodes 523 through 528 exposed at the bottom of supporters 541 through 544.

The reason why draw-out electrodes 504 through 509 and 523 through 528 are formed as a part of free vibrating sections 545 through 547 is as follows: such a structure can avoid cancellation of the drawn out electric charge due to stress distribution in free vibrating sections 545 through 547. in the structure above, for example, each width of draw-out electrodes 504 and 505 is determined less than one-fifth of that of main electrode 501.

Free vibrating sections 545, 546, and 547 have lengths of L3, L2, and L1, respectively, and in which L3 is the longest, and L1 is the shortest. Free vibrating sections 545 through 547 are electrically separated each other.

Figure 2A:
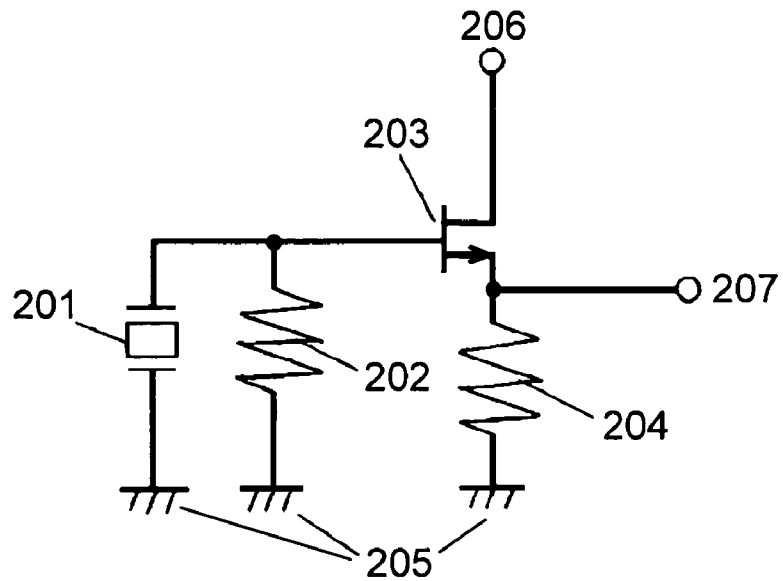
FIG. 2A shows a circuit diagram of an acceleration sensor of the first embodiment.

FIG. 2A shows the circuit diagram of acceleration sensors 101 through 103 shown in FIG. 1. Acceleration sensor element 201 is the one the same as shown in FIGS. 5A through 5D. One of draw-out electrodes 523 and 524 shown in FIGS. 5A through 5D is connected to ground 205 of FIG. 2A. On the other hand, one of draw-out electrodes 504 and 505 shown in FIGS. 5A through 5D is connected to resistor 202 of FIG. 2A. The electric charge obtained from draw-out electrode 504 or 505 is converted through resistor 202 into current. Besides, feeding the current through resistor 202 allows resistor 202 to generate voltage. In the case that resistor 202 is required to have large resistance value more than 1 MΩ, employing field-effect transistor (FET) 203 allows the circuit to have lower impedance. The source of FET 203 is connected, through terminal 206, to the positive side of a power-supplying unit; the gate is connected to the acceleration sensor element 201 and resistor 202; and the drain is connected to resistor 204. The other terminal of resistor 204 is connected to ground 205. The potential of the drain is taken out through terminal 207. Forming the circuit like this allows terminal 207 to have lower output impedance.

The acceleration sensor element shown in FIGS. 5A through 5D also has free vibrating sections 546 and 547. Each signal obtained from the two sections is similarly processed, as shown in FIG. 2A.

A signal from terminal 207 is fed to the corresponding one of switches 106 through 108.

In the embodiment, ID numbers 1 through 3 are assigned to the acceleration sensors having free vibrating sections 545 through 547, respectively, and a letter "S" indicates the ID number: S=1 in acceleration sensor 101 containing free vibrating section 545; S=2 in acceleration sensor 102 containing free vibrating section 546; and S=3 in acceleration sensor 103 containing free vibrating section 547. Similarly, a letter "N" represents the total number of acceleration sensors: N=3 in the acceleration sensors shown in FIGS. 5A through 5D.

Although the explanation above introduces the structure in which i) generating current by moving the electric charge obtained from one of draw-out electrodes 504 and 505; ii) converting the current into voltage by feeding through resistor 202; and then iii) amplifying the voltage, it is not limited thereto: the structure in which current is directly amplified is also acceptable.

Acceleration sensor element 201 generally bears capacitance—working the capacitance with resistor 202 inevitably forms a filter that cuts off low band frequencies. Therefore, the signals generated in acceleration sensor element 201 are decreased in low frequency band. In this case, the low-band cut-off frequency, "Fc" is given by the expression below.

$$Fc = 1/(2\pi \times R \times Cs) \qquad \text{(Expression. 1)},$$

where, Cs represents capacitance of acceleration sensor element 201; R represents resistance of resistor 202.

Figure 3:
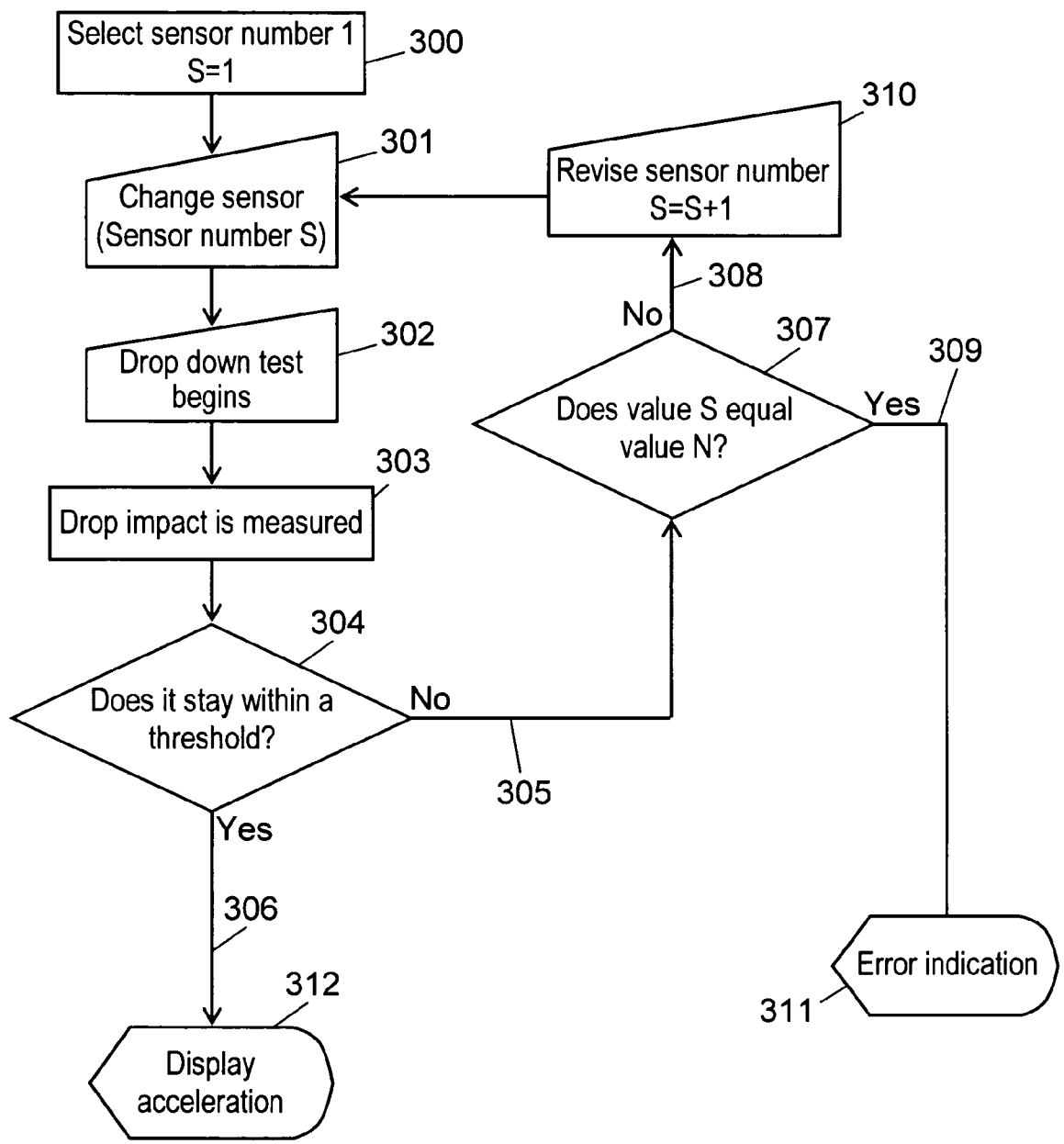
FIG. 3 is a flow chart illustrating the routine of detecting drop impact acceleration in a drop impact measuring system of the first and second embodiments.

FIG. 3 is a flow chart illustrating the routine of measuring drop impact in the circuit shown in FIG. 1. In the first step 300, an acceleration sensor including the free vibrating section with the highest sensibility and the lowest resonance frequency is selected from free vibrating sections 545 through 547 of different lengths shown in FIGS. 5A through 5D; acceleration sensor 101 including free vibrating section 545 can provide the highest sensibility and the lowest resonance frequency, that is, "S" takes on 1.

In step 301, among switches 106 through 108, only one switch associated with the acceleration sensor selected in step 300 is closed, whereby sensor switching is performed. At the moment, since "S" retains the value of 1, only switch 106 of FIG. 1 is closed.

In step 302, the drop down test begins.

In step 303, drop impact caused by the drop-down is measured. Amplifying circuit 104 amplifies signals from acceleration sensor 101 generated by the drop impact and then outputs the measured result (i.e., impact acceleration) through terminal 110 shown in FIG. 1

In step 304, logic circuit 105 evaluates whether the output signal from amplifying circuit 104 stays within a threshold or not, and whether resonance occurs or not.

In step 306, if the impact acceleration stays within the threshold, the acceleration is displayed in step 312. A display for showing the impact acceleration is not shown in FIG. 1.

On the other hand, if the impact acceleration exceeds the threshold, the procedure goes to step 307. In step 307, the value currently stored in S is compared with the value stored in N.

If the comparison finds that the value of S equals to that of N—which means that each of the output signals generated from free vibrating sections 545 through 547 shown in FIGS. 5A through 5D via amplifying circuit 104 exceeds the threshold, the procedure goes to step 311, where an error indication is shown on the display.

On the other hand, if S does not reach N, the procedure goes to step 310 where the value of S (that indicates a sensor number) is updated. That is, S is incremented by 1 in step 310, and then the procedure goes back to step 301. According to the updated S, next acceleration sensor is selected in step 301, and the drop impact measurement is resumed from step 302.

Figure 4:
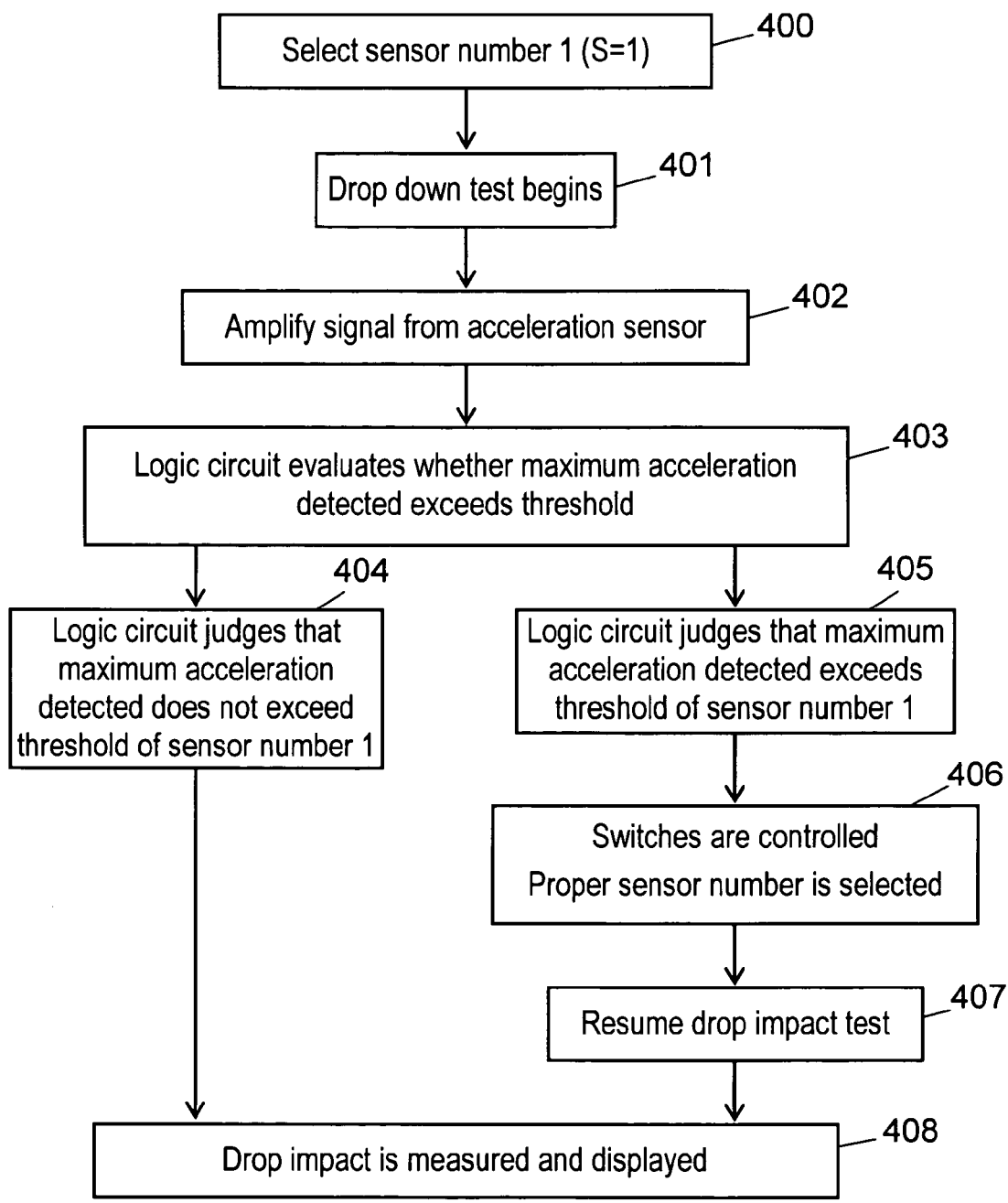
FIG. 4 is another flow chart illustrating the routine of detecting drop impact acceleration in a drop impact measuring system of the first and second embodiments.

FIG. 4 is another flow chart illustrating the routine of measuring drop impact in the circuit shown in FIG. 1. According to the flow chart shown in FIG. 3, if the result of the drop impact measurement obtained at step 303 exceeds the threshold of S representing a sensor number, the value of S is incremented by 1 in step 310, and then the drop-impact measurement is resumed at step 302. On the other hand, in the flow chart of FIG. 4, even if the first result of the measurement exceeds the threshold of S, the logic circuit evaluates output signals to find a proper sensor number, and then the drop impact measurement is resumed with the acceleration sensor corresponding to the sensor number.

In step 400, S initially takes on 1, and the drop impact test begins at step 401. Next, in step 402, amplifying circuit 104 amplifies the output signal of acceleration sensor 101 that has been entered through switch 106.

In step 403, logic circuit 105 evaluates whether the output signal from amplifying circuit 104 stays within a threshold or not, and whether resonance occurs or not.

In step 404, if the logic circuit evaluates that the impact acceleration stays within a threshold, the acceleration is displayed in step 408. A display for showing the impact acceleration is not shown in FIG. 1.

On the other hand, if the impact acceleration exceeds the threshold, logic circuit 105 selects a proper sensor number according to the output signal of amplifying circuit 104 in step 406.

In step 407, a switch corresponding to the sensor number selected above is closed to resume the drop impact test.

In step 408, the drop impact is measured and displayed.

An acceleration sensor for detecting drop impact is required to have differently ranged resonance frequencies, that is, desirably to have various frequencies, not only one.

In the acceleration sensor element shown in FIGS. 5A through 5D, suppose that "fr" represents the resonance frequency; "L" represents the length of the free vibrating sec tion; "t" represents the thickness; and "α" represents a constant, "fr" is given by the expression below:

$$Fr \propto \alpha \times T/L^2 \qquad \text{(Expression 2)}.$$

That is, the resonance frequency "fr" varies inversely with the square of the length of the free vibrating section. The acceleration sensor element shown in FIGS. 5A through 5D has free vibrating sections 545 through 547 of different lengths, thereby offering various resonance frequencies. The acceleration sensor element shown in FIGS. 5A through 5D is thus ready for various resonance frequencies.

Employing such structured acceleration sensor element for a drop impact measuring system can easily detect impact acceleration, even in the case that a resonance frequency at the drop down of an object is unpredictable in advance. Accordingly, it will contribute to easy structural design of the housing.

Each of FIGS. 7A through 7C, and FIGS. 8A through 8D shows an acceleration sensor element having a cantilever beam structure.

Figure 7A:
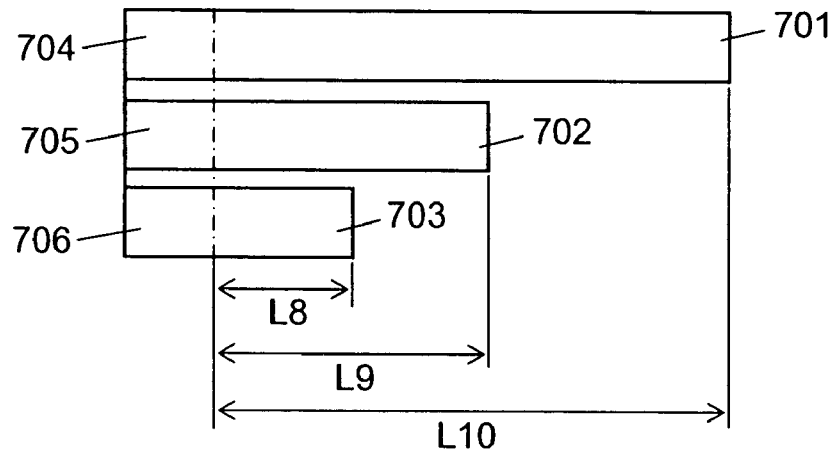
FIG. 7A shows a top view of an acceleration sensor element having a cantilever beam structure in accordance with the first embodiment.
Figure 7B:
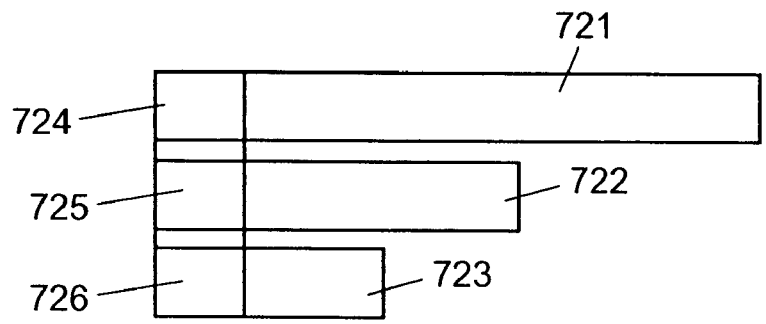
FIG. 7B shows a bottom view of the acceleration sensor element having a cantilever beam structure in accordance with the first embodiment.
Figure 7C:
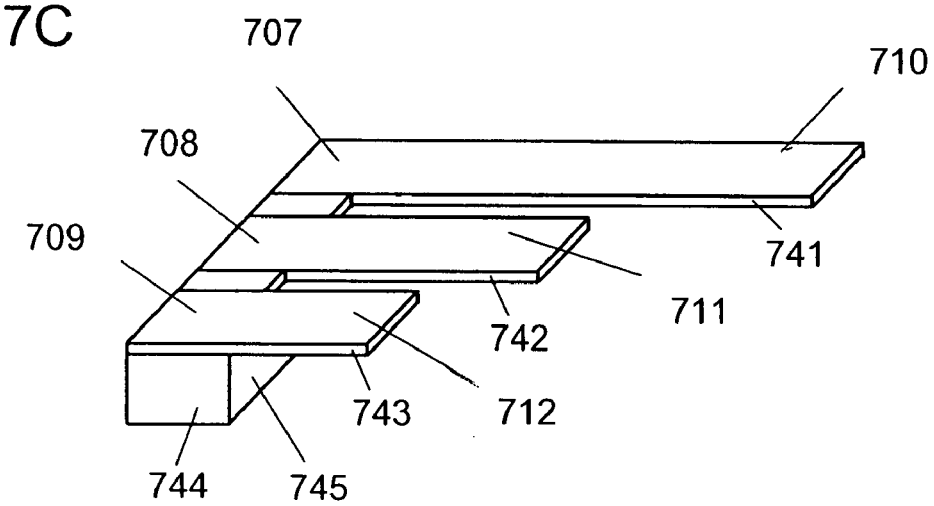
FIG. 7C shows a perspective view of the acceleration sensor element having a cantilever beam structure in accordance with the first embodiment.

FIG. 7A is a top view, FIG. 7B is a side view, and FIG. 7C is a perspective view. The structures, in which supporter 744 holds one end (i.e., the fixed end/fixed portion 707, 708 and 709) of each of free vibrating sections 741 through 743, forms into a cantilever beam. Free vibrating sections 741, 742, and 743 have fixed portions 707, 708 and 709 and free vibrating portions 710, 711 and 712 and include main electrodes 701, 702, and 703 on the upper surfaces thereof, and main electrodes 721, 722, and 723 on the lower surfaces thereof, respectively. Draw-out electrodes 724, 725, and 726, which are formed on the bottom of supporter 744, are electrically connected with main electrodes 721, 722, and 723, respectively.

Figure 8A:
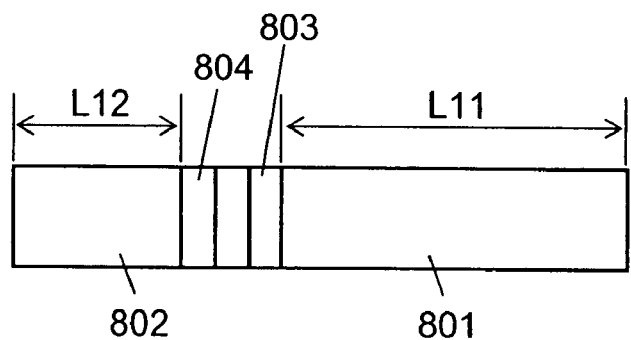
FIG. 8A shows a top view of another acceleration sensor element having a cantilever beam structure in accordance with the first embodiment.
Figure 8B:
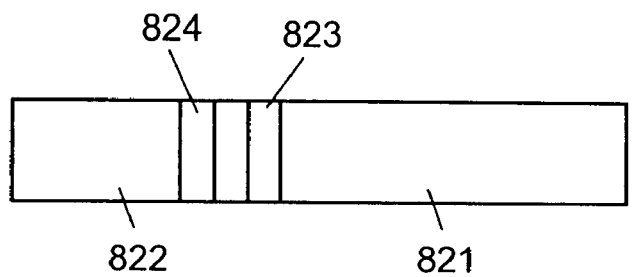
FIG. 8B shows a bottom view of the acceleration sensor element having a cantilever beam structure in accordance with the first embodiment.
Figure 8C:
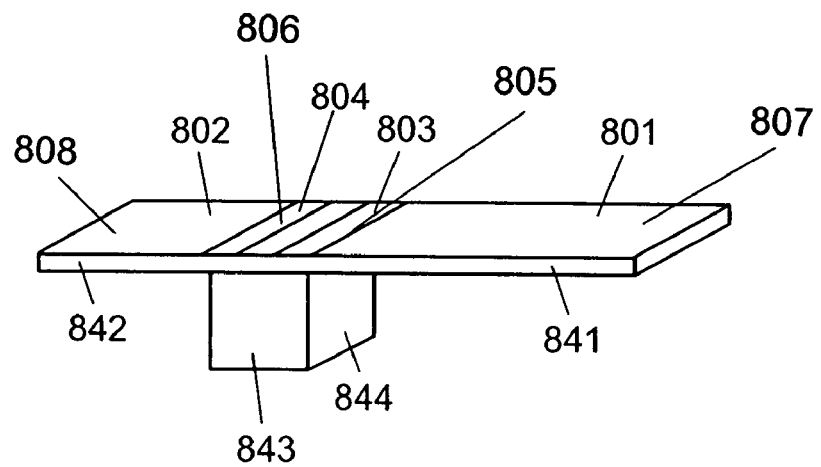
FIG. 8C shows a perspective view of the acceleration sensor element having a cantilever beam structure in accordance with the first embodiment.

Each of FIGS. 8A through 8D shows another acceleration sensor element having the cantilever beam structure. FIG. 8A is a top view, FIG. 8B is a bottom view, and Fig. 8C is a perspective view. The structure, in which supporter 843 holds one end (the fixed portion 805 and 806) of each free vibrating sections 841 and 842, forms into a cantilever beam. Free vibrating section 841 has fixed portion 805 and free vibrating portion 807 and includes main electrode 801 on the upper surface thereof, and main electrode 821 on the lower surface thereof. Similarly, free vibrating section 842 has fixed portion 806 and free vibrating portion 808 and includes main electrode 802 on the upper surface thereof, and main electrode 822 on the lower surface thereof. Draw-out electrodes 803 and 804 are electrically connected with main electrodes 801 and 802, respectively. Draw-out electrode 823, which is formed on the bottom of supporter 843, runs across side 844 of the supporter and reaches main electrode 821 to have electric connections. Similarly, draw-out electrode 824, which is also formed on the bottom of supporter 843, runs across the side opposite to side 844 of the supporter and reaches main electrode 822 to have electric connections. As shown in FIGS. 8A-8C, free vibrating sections 841 and 842 are opposed to each other.

When comparisons are made between the acceleration sensor element formed into a cantilever beam structure shown in FIGS. 7A through 7C and FIGS. 8A through 8C; and the acceleration sensor element formed into a both ends-supported beam structure shown in FIGS. 5A through 5D, the cantilever beam structure generates four to five times more amount of output electrical charge than the both ends-supported beam structure does, provided they have same dimensions. Therefore, amplifying circuit 104 of FIG. 1, which is necessary for the acceleration sensor element having the both ends-supported beam shown in FIGS. 5A through 5D, can be eliminated by using the cantilever beam structure. Eliminating the amplifying circuit can provide a low-cost drop impact measuring system. Besides, the parallel arrangement of free vibrating sections 741 through 743 allows the whole structure of the acceleration sensor element to be compact, accordingly providing a downsized drop impact measuring system.

Employing the structure explained in the first embodiment can provide the drop impact measuring system that easily measures an impact acceleration of even more than 1000 G having great variations in resonance frequency. At the same time, the structure of the embodiment also provides an acceleration sensor element capable of detecting impact acceleration of various resonance frequencies.

Second Exemplary Embodiment

Figure 2B:
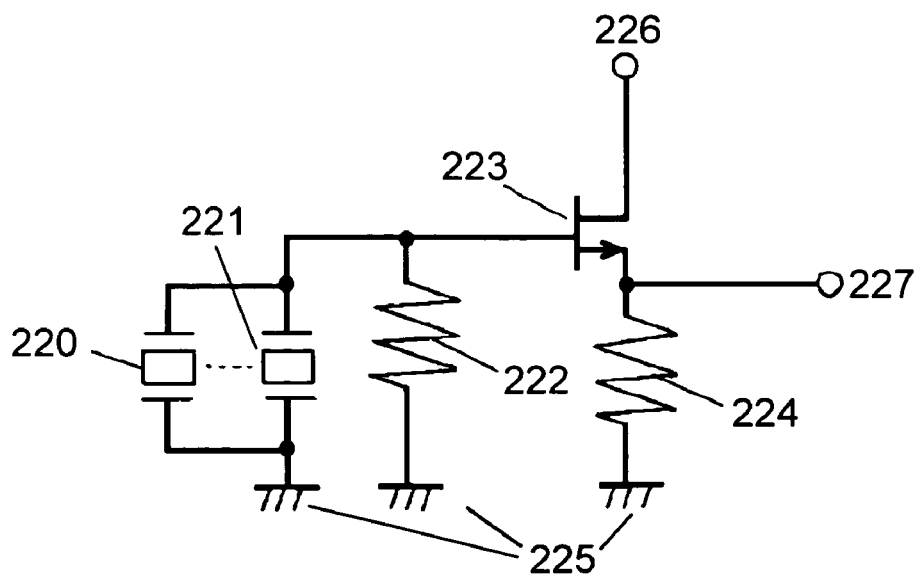
FIG. 2B shows a circuit diagram of an acceleration sensor of the second embodiment.

FIG. 1 also shows a circuit diagram of the drop impact measuring system of the second embodiment. FIG. 2B shows a circuit diagram of the acceleration sensor of the second embodiment. FIGS. 3 and 4 are flow charts illustrating the routine of detecting drop impact acceleration in the drop impact measuring system of the second embodiment. Each of FIGS. 6A through 6C shows an acceleration sensor element having a structure of cantilever beam of the second embodiment.

Figure 6A:
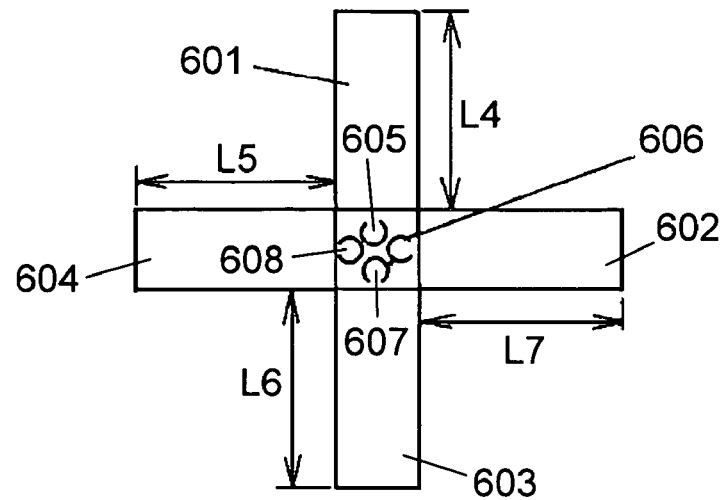
FIG. 6A shows a top view of an acceleration sensor element having a cantilever beam structure in accordance with the second embodiment.
Figure 6B:
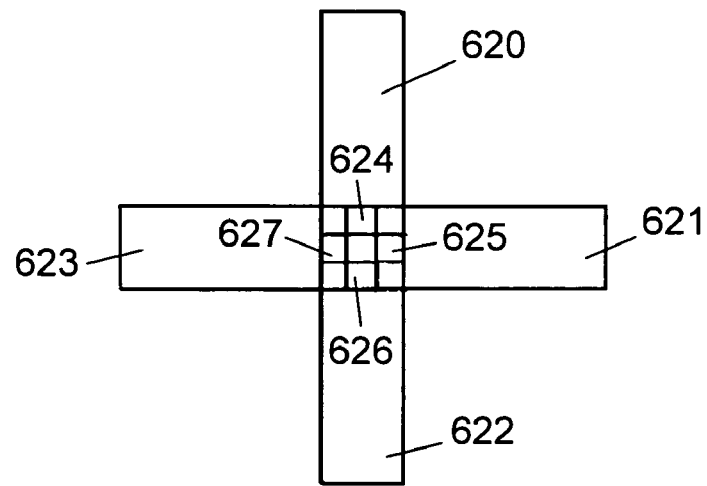
FIG. 6B shows a bottom view of the acceleration sensor element having a cantilever beam structure in accordance with the second embodiment.
Figure 6C:
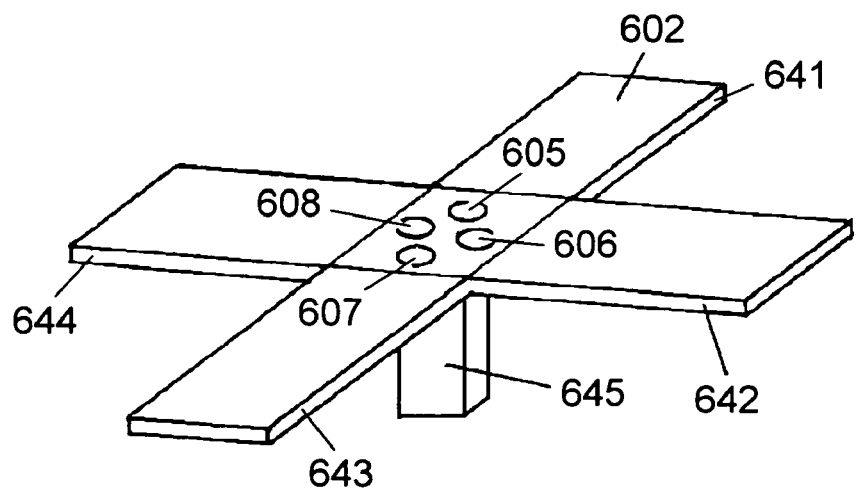
FIG. 6C shows a perspective view of the acceleration sensor element having a cantilever beam structure in accordance with the second embodiment.

FIG. 6A is a top view, FIG. 6B is a bottom view, and FIG. 6C is a perspective view. Each one end of free vibrating sections 641 through 644 are supportably fixed by supporter 645. Free vibrating sections 641, 642, 643, and 644 have main electrodes 601, 602, 603, and 604 on the upper surfaces thereof; and have main electrodes 620, 621, 622, and 623 on the lower surfaces thereof, respectively. Main electrodes 601, 602, 603, and 604 are electrically connected with draw-out electrodes 605, 606, 607, and 608, respectively. Similarly, main electrodes 620, 621, 622, and 623 are electrically connected with draw-out electrodes 624, 625, 626, and 627, respectively. Draw-out electrodes 624 through 627 are exposed from the bottom of supporter 645. Free vibrating sections 641, 642, 643, and 644 are of the same length, which are represented by L4, L5, L6, and L7, respectively.

Using the acceleration sensor element shown in FIGS. 6A through 6C, the acceleration sensor is formed, as shown in FIG. 2B. That is, acceleration sensor element 220 is formed of free vibrating section 641; main electrodes 601 and 620; and draw-out electrodes 605 and 624. Of four acceleration sensor elements shown in FIGS. 6A through 6C, one is used for sensor element 220; any one of the rest three is to be employed for sensor element 221. Draw-out electrodes 624 through 627 are connected to ground 225. On the other hand, draw-out electrodes 605 through 608, which are electrically connected in parallel, and then connected to resistor 222. Resistors 222 and 224, FET223, terminals 226 and 227 shown in FIG. 2B act the same as resistors 202 and 204, FET203, terminals 206 and 207 shown in FIG. 2A, respectively, therefore the explanation of the components above will be omitted. Such structured acceleration sensor serves as acceleration sensor 101 shown in FIG. 1.

Although acceleration sensors 102 and 103 are formed in the same manner with sensor 101, each acceleration sensor element used for these three sensors has differently ranged resonance frequency. That is, the acceleration sensor can offer various resonance frequencies.

To measure greater drop impact acceleration, miniaturizing the acceleration sensor element and increasing mechanical strength seems to be an effective way. According to a prior-art acceleration sensor element, however, miniaturization of a sensor element has lowered electric capacity and thereby degraded durability of noise characteristics of the sensor element itself. Whereas the sensor element introduced in the second embodiment, by virtue of the structure in which the free vibrating sections of same resonance frequencies are electrically connected in parallel, has no decrease in electric capacity if the sensor element itself is miniaturized. Therefore, the structure described in the second embodiment can provide a high-noise-durability acceleration sensor element and a drop impact measuring system using the sensor element.

A prior-art acceleration sensor element, as described above, lowers electric capacity as it is downsized. As a result, the "Fc" given by the Expression 1, which represents low-band cut-off frequency, takes on a large value. Whereas the acceleration sensor element of the second embodiment has no decrease in electric capacity, thereby keeping the low-band cut-off frequency "Fc" from getting high.

Although the acceleration sensor of the second embodiment is formed of the acceleration sensor element having the shape illustrated in FIGS. 6A through 6C, it is not limited thereto: the similar effect can be obtained by the structure having free vibrating sections 741, 742, and 743 (FIGS. 7A through 7C) of same lengths, i.e., L10=L9=L8; the structure having free vibrating sections 841 and 842 (FIGS. 8A through 8C) of same lengths, i.e., L11=L12; or the structure having free vibrating sections 545, 546, and 547 (FIGS. 5A through 5D) of same lengths, i.e., L3=L2=L1.

INDUSTRIAL APPLICABILITY

The drop impact measuring system and the acceleration sensor element employed for the system of the present invention can cope well with wide ranged resonance frequencies and great impact acceleration. Besides, the acceleration sensor element can be miniaturized and improved in durability of noise characteristics.

The invention claimed is:

1. A bimorph-type acceleration sensor element, which is used for a bimorph-type acceleration sensor, comprising:
    a common supporter;
    a plurality of bimorph free vibrating sections having a cantilever beam structure, each of the free vibrating sections having a first portion that is in contact with the common supporter and a second portion that is not in contact with the common supporter;
    a main electrode on a top surface of each of said free vibrating sections;
    a further main electrode on a bottom surface of each of said free vibrating sections;
    a set of draw-out electrodes corresponding to each of said free vibrating sections and for drawing out electric charge from the vibrating sections, each respective draw-out electrode of the set of draw-out electrodes being electrically connected to a corresponding one of the main electrode or the further main electrode, the draw-out electrodes of each respective set being electrically isolated from each other, wherein:
    the second portion of a first one of the plurality of free vibrating sections extends from one edge of the common supporter and the second portion of a second one of the plurality of free vibrating sections extends from an opposite edge of the common supporter, the second portions of the first and second ones of the plurality of free vibrating sections defining a set of opposed second portions, and
    the first portion of the first one of the plurality of free vibrating sections is disposed in a first region adjacent to the one edge of the common supporter and the first portion of a second one of the plurality of free vibrating sections is disposed in a second region adjacent to the opposite edge of the common supporter, the first portions of the first and second ones of the plurality of free vibrating sections defining a set of opposed first portions such that opposed first portions are closer to each other than opposed second portions are closer to each other.

2. The bimorph-type acceleration sensor element of claim 1, wherein the plurality of the free vibrating sections are of different lengths and are electrically independent.

3. The bimorph-type acceleration sensor element of claim 1, wherein the plurality of the free vibrating sections are of identical length and are electrically connected in parallel.

4. The sensor element according to claim 1, wherein the draw-out electrodes of the set of draw-out electrodes are not electrically connected together.

5. The sensor element according to claim 1, wherein:

the common supporter includes a plurality of side regions and a bottom region; and a first one of the draw-out electrodes of each respective set of draw-out electrodes is electrically connected to a respectively different one of the further main electrodes of the plurality of free vibrating sections and is disposed on a respectively different one of the side regions of the common supporter such that the first one of the draw-out electrodes of each respective set continues from the respectively different one of the side regions onto the bottom region of the common supporter to expose the first one of the of the draw-out electrodes of each respective set at the bottom region of the common supporter.

* * * * *